(12) United States Patent
Alexander

(10) Patent No.: US 8,012,111 B2
(45) Date of Patent: Sep. 6, 2011

(54) ORAL HYGIENE DEVICE

(75) Inventor: J. Byron Alexander, Berkeley Lake, GA (US)

(73) Assignee: Carolyn Marlow Ream, Berkeley Lake, GA (US)

( * ) Notice: Subject to any disclaimer, the term of this patent is extended or adjusted under 35 U.S.C. 154(b) by 891 days.

(21) Appl. No.: 11/962,960

(22) Filed: Dec. 21, 2007

(65) Prior Publication Data

US 2009/0163839 A1    Jun. 25, 2009

(51) Int. Cl.
*A61H 13/00* (2006.01)

(52) U.S. Cl. .......... 601/162; 601/160; 601/165; 433/80; 433/84

(58) Field of Classification Search .......... 601/160–165; 137/595; 251/208; 433/80, 215, 229, 84, 433/85, 91, 92

See application file for complete search history.

(56) References Cited

U.S. PATENT DOCUMENTS

| | | | | |
|---|---|---|---|---|
| 2,829,645 A | * | 4/1958 | Matteson | 604/150 |
| 4,043,337 A | * | 8/1977 | Baugher | 604/150 |
| 4,753,260 A | * | 6/1988 | Gibbs | 137/14 |
| 4,941,459 A | | 7/1990 | Mathur | |
| 4,942,870 A | | 7/1990 | Damien | |
| 5,095,893 A | * | 3/1992 | Rawden, Jr. | 601/165 |
| 5,113,906 A | * | 5/1992 | Hogner | 137/595 |
| 5,220,914 A | * | 6/1993 | Thompson | 601/155 |
| 6,247,929 B1 | * | 6/2001 | Bachman et al. | 433/80 |
| 6,648,017 B2 | * | 11/2003 | Lamas et al. | 137/595 |
| 6,749,090 B2 | * | 6/2004 | Bailey | 222/175 |
| 6,835,181 B2 | | 12/2004 | Hippensteel | |
| 2004/0045107 A1 | | 3/2004 | Egeresi | |
| 2006/0010624 A1 | * | 1/2006 | Cleland | 15/29 |
| 2006/0048791 A1 | * | 3/2006 | Mehes et al. | 132/310 |
| 2008/0078021 A1 | * | 4/2008 | Welch | 4/675 |
| 2008/0135115 A1 | * | 6/2008 | Johansson et al. | 137/595 |
| 2009/0053672 A1 | * | 2/2009 | Cornelius | 433/80 |

* cited by examiner

*Primary Examiner* — Danton DeMille
*Assistant Examiner* — Si Lee
(74) *Attorney, Agent, or Firm* — Dale J. Ream

(57) ABSTRACT

An oral hygiene device for use with a sink having hot and cold water lines includes a storage mount and a housing removably coupled thereto. The housing includes hot and cold water inputs and an outlet. The housing also includes first and second channels coupling the inputs to the outlet. The device includes piping tees and flexible tubing for connection to a sink's water lines. The device includes adjustable temperature valves in the first and second channels, respectively, for regulating amounts of hot and cold water passing through the channels. An adjustable volume valve is included for determining a volume of water exiting the outlet. The storage mount may be installed on a sink adjacent the faucet so that the oral hygiene device is a permanent fixture.

7 Claims, 5 Drawing Sheets

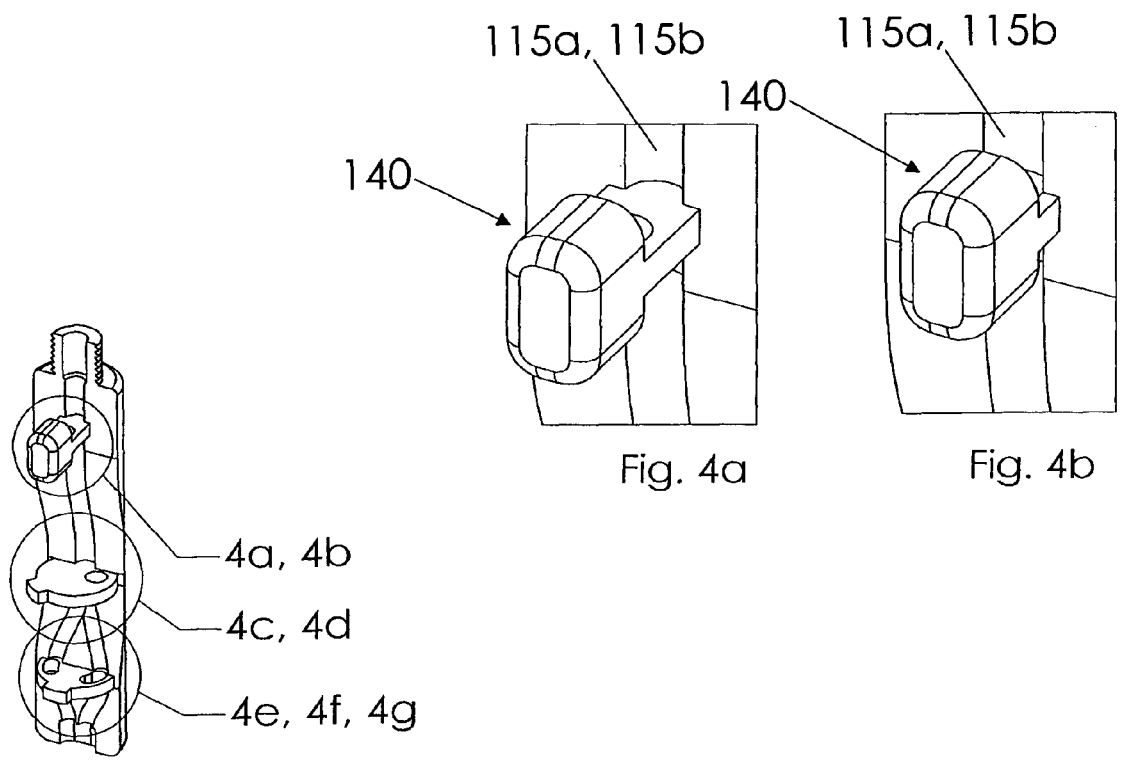
Fig. 4a   Fig. 4b
Fig. 4
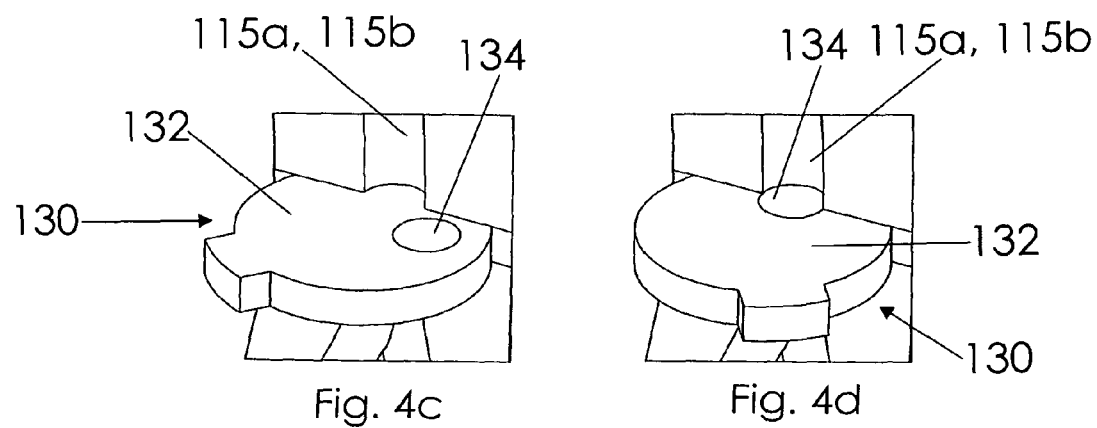
Fig. 4c   Fig. 4d

ORAL HYGIENE DEVICE

BACKGROUND OF THE INVENTION

The present invention relates generally to oral hygiene devices and, more particularly, to an oral hygiene device that is installed as a permanent fixture in a bathroom sink environment.

Thorough dental care is a very important part of one's health and personal hygiene and, while brushing and flossing are the primary and traditional methods for keeping one's teeth clean, there are other devices that may aid or contribute to in maximizing one's oral health. Oral irrigators may help keep teeth clean by shooting a jet of water into areas that may be difficult to reach with a toothbrush.

Various devices have been proposed in the art for irrigating a person's oral cavity and for loosening food particles or plaque from one's teeth using high pressure water streams. Although assumably effective for their intended purposes, the existing devices and patent proposals do not provide a permanent sink fixture and offers improved control over the volume, velocity, and temperature of water flowing through the device.

Therefore, it would be desirable to have an oral hygiene device that provides a permanent sink fixture that satisfies the limitations or disadvantages of the existing devices and proposals in the prior art.

SUMMARY OF THE INVENTION

An oral hygiene device for use with a sink having a hot water and a cold water line according to the present invention includes a storage mount and a housing removably coupled to the storage mount. The housing includes a hot water input and a cold water input and an outlet, the housing having a first channel coupling the hot water input to the outlet and a second channel coupling the cold water input to the outlet. A portion of the first channel corresponds with a portion of the second channel.

The oral hygiene device includes a first piping tee coupled to the hot water line and a second piping tee coupled to the cold water line. In addition the device includes a flexible tube connecting the first piping tee to the housing hot water input and a flexible tube connecting the second piping tee to the housing cold water input. An temperature valve is positioned in the first channel for determining an amount of hot water passing through the first channel. Another adjustable temperature valve is positioned in the second channel for determining an amount of cold water passing through the second channel. In addition, the device includes an adjustable volume valve for determining an amount of water exiting the outlet, the volume valve being situated in the first channel portion that corresponds with the second channel portion.

Therefore, a general object of this invention is to provide an oral hygiene device that may be installed as a permanent sink fixture for meeting the oral hygiene needs of a user.

Another object of this invention is to provide an oral hygiene device, as aforesaid, that is installed adjacent a sink faucet and is coupled directly to the water lines of the sink.

Still another object of this invention is to provide an oral hygiene device, as aforesaid, that provides user controls for individually controlling the volume, velocity, and temperature of water flowing therethrough.

Yet another object of this invention is to provide an oral hygiene device, as aforesaid, that is easy to install, convenient to use, and economical to manufacture.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 4 is a perspective view of a portion of the housing as in FIG. 3;

FIGS. 4a and 4b are isolated views on an enlarged scale taken from a portion of FIG. 4 showing an on/off button in various configurations;

FIGS. 4c and 4d are isolated views on an enlarged scale taken from a portion of FIG. 4 showing an adjustable volume disc valve in various configurations;

DESCRIPTION OF THE PREFERRED EMBODIMENT

An oral hygiene device 100 according to the present invention will now be described in detail with reference to FIGS. 1a through 4g of the accompanying drawings. More particularly, according to the current invention, an oral hygiene device 100 includes a housing 110 and a temperature control 120.

Figure 3:
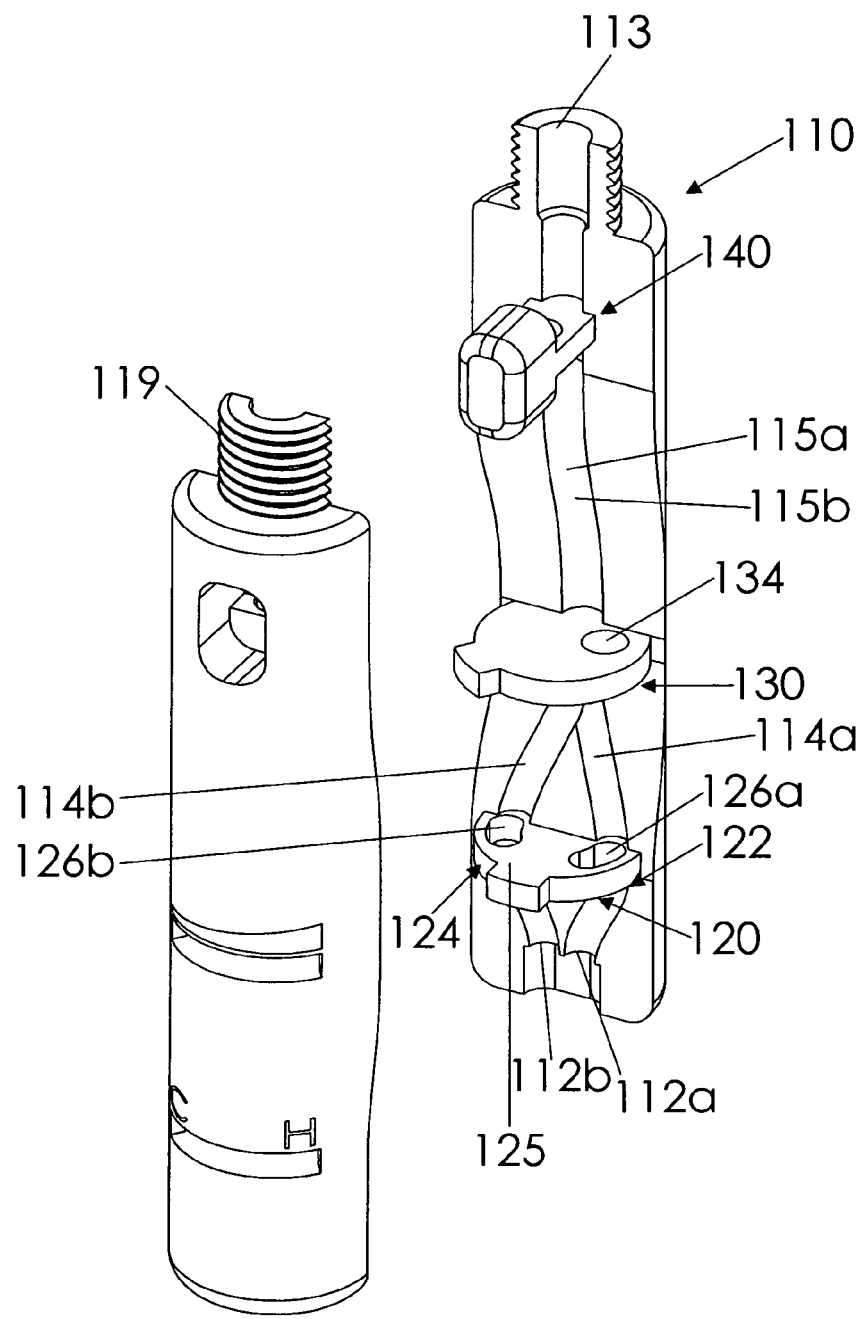
FIG. 3 is an exploded view of the oral hygiene device housing.

As shown in FIG. 3, the housing 110 has a hot water input 112a, a cold water input 112b, and an outlet 113. A first channel 114a couples the hot water input 112a to the outlet 113, and a second channel 114b couples the cold water input 112b to the outlet 113. A portion 115a of the first channel 114a corresponds with a portion 115b of the second channel 114b, or in other words, the portion 115a of the first channel 114a is unitary with the portion 115b of the second channel 114b.

Figure 4E:
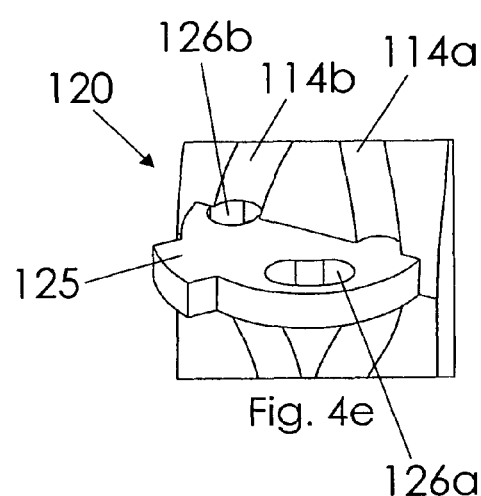
FIGS. 4e, 4f, and 4g are isolated views on an enlarged scale taken from a portion of FIG. 4 showing a temperature control disc in various configurations.
Figure 4F:
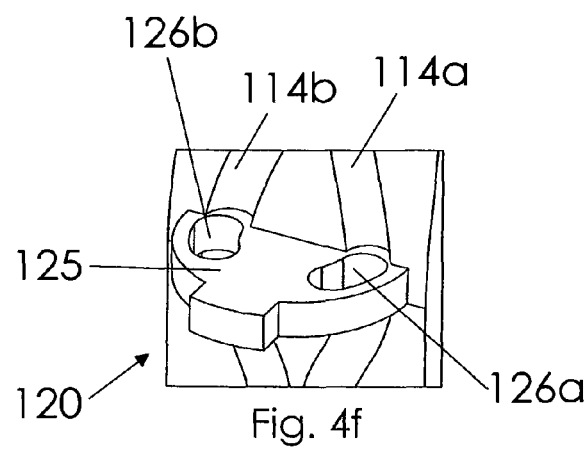
Figure 4G:
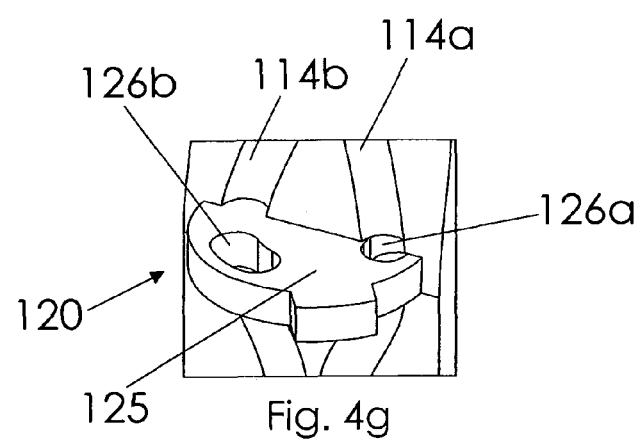

The temperature control 120 includes an adjustable temperature valve 122 in the first channel 114a determining an amount of hot water passing through the first channel 114a and an adjustable temperature valve 124 in the second channel 114b determining an amount of cold water passing through the second channel 114b. According to one embodiment, as shown in FIG. 3, the temperature control 120 more particularly comprises a rotatable disc 125 having first and second holes 126a, 126b. The first hole 126a corresponds to the first channel 114a and the second hole 126b corresponds to the second channel 114b when the disc 125 is at a first position 125a (FIG. 4f). Rotation of the disc 125 in one direction 125b causes the first hole 126a to separate from the first channel 114a and the disc 125 to obstruct the first channel 114a, as shown in FIG. 4e. Rotation of the disc 125 in another direction 125c causes the second hole 126b to separate from the second channel 114b and the disc 125 to obstruct the second channel 114b, as shown in FIG. 4g.

An adjustable volume valve 130 may be included to determine an amount of water that exits the outlet 113. As shown in FIG. 3, the valve 130 may be in the overlapping channel portions 115a, 115b. In one embodiment, the valve 130 comprises a rotatable disc 132 having a hole 134 that selectively interacts with the overlapping channel portions 115a, 115b. Rotation of the disc 132 from the position shown in FIG. 4d causes the hole 134 to separate from the overlapping channel portions 115a, 115b and the disc 132 to obstruct the overlapping channel portions 115a, 115b, as shown in FIG. 4c.

As shown in FIGS. 3, 4a, and 4b, an on-off valve 140 may be included in the housing 110 to selectively restrain water from exiting the outlet 113. In other words, the on-off valve 140 may be movable between a position entirely blocking water from exiting the outlet 113 (FIG. 4a) and a position allowing water to exit the outlet 113 (FIG. 4b) without further affecting or adjusting the amount of water flow.

A nozzle 150 (FIG. 2) may be operatively coupled to the housing 110, in either a permanent or removable manner. The housing 110 may include threads 119, as shown in FIG. 3 for example, to couple the nozzle 150 to the housing 110. The nozzle 150 may provide a channel 152 extending from the outlet 113 to direct water flow from the outlet 113 through the nozzle 150, and the nozzle may have an elongate configuration 155 for positioning inside a user's mouth.

Figure 1:
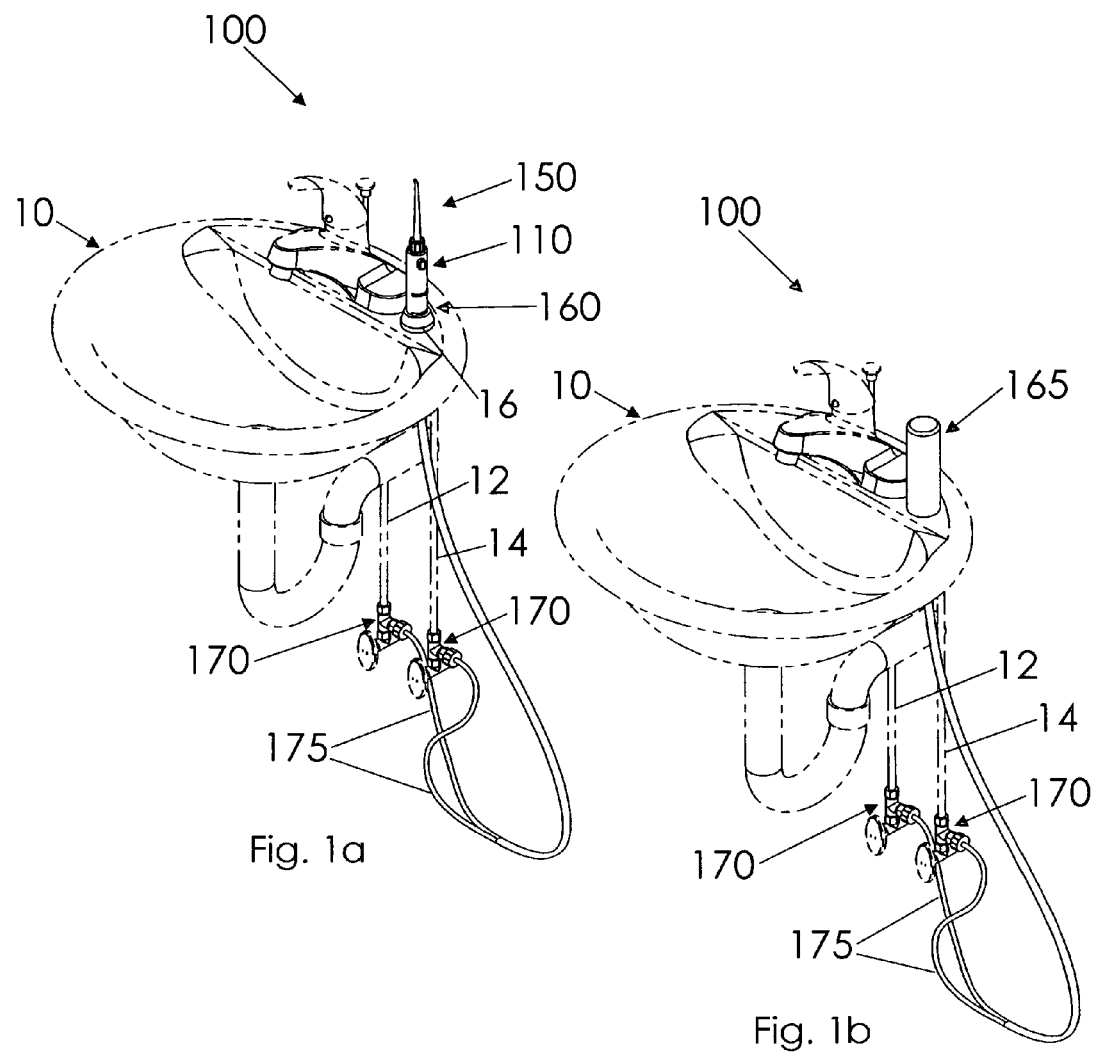
FIG. 1a is a perspective view of an oral hygiene device according to the present invention installed on a sink.
FIG. 1b is another perspective view of the oral hygiene device in use with a storage sleeve.
Figure 2:
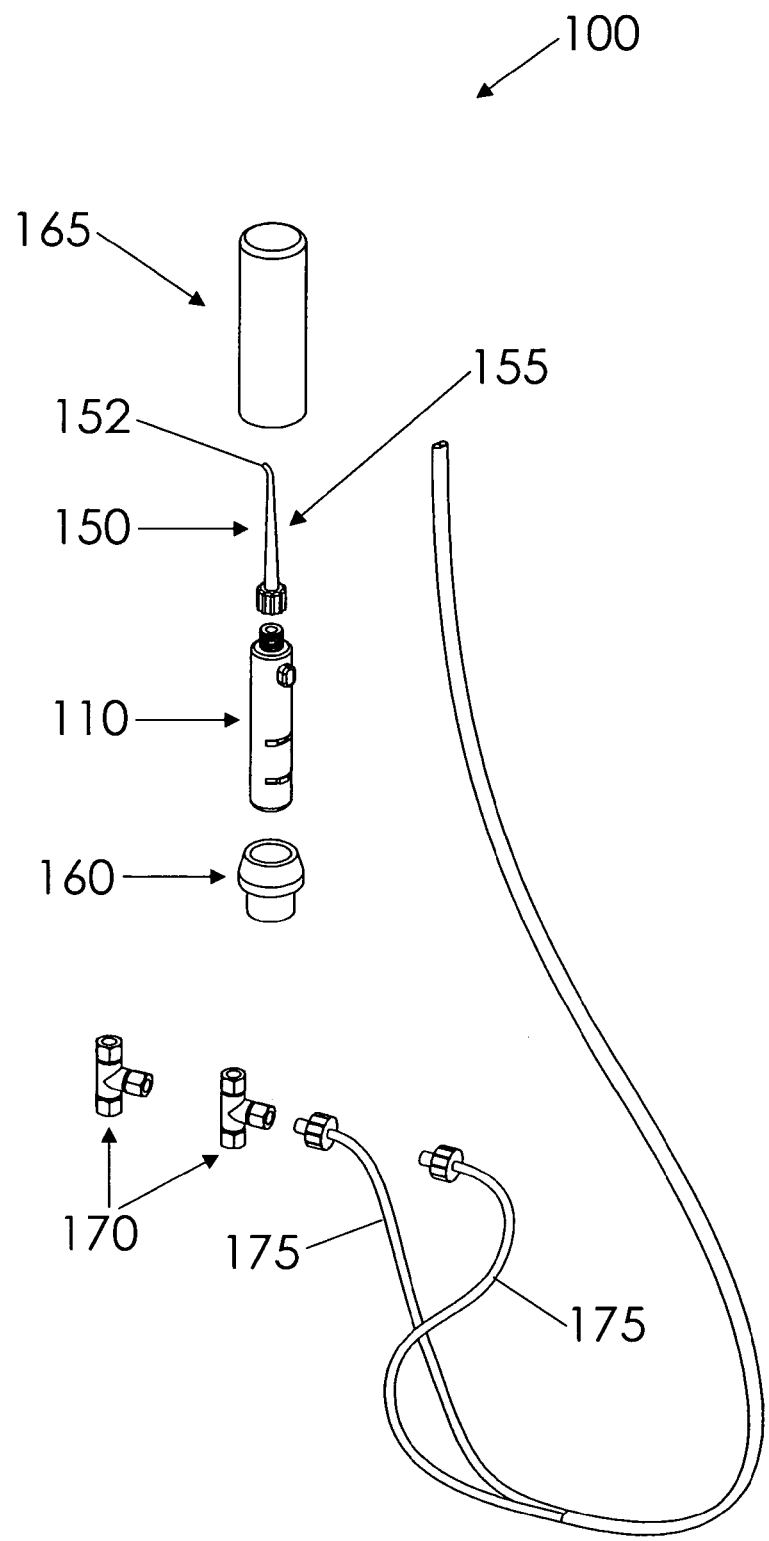
FIG. 2 is an exploded view of the oral hygiene device as in FIG. 1.

As shown in FIG. 2, a storage mount 160 may be included, and the housing 110 may be removably coupled to the storage mount 160. A sleeve 165 may be selectively coupled to the storage mount 160 to enclose the housing 110 when the housing is coupled to the storage mount (FIG. 1b). In some embodiments, the nozzle 150 may need to be removed before the sleeve 165 is coupled to the storage mount 160, while in other embodiments the sleeve 165 may be coupled to the storage mount 160 while the nozzle 150 is attached to the housing 110.

To use the oral hygiene device 100 with a sink 10 having a hot water line 12, a cold water line 14, and a mounting hole 16, piping tees 170 may be included for coupling to the hot and cold water lines 12, 14, and flexible tubing 175 may connect the piping tees 170 to the hot and cold water inputs 112a, 112b. More particularly, flexible tubing 175 may connect the piping tee 170 coupled to the hot water line 12 to the hot water input 112a, and flexible tubing 175 may connect the piping tee 170 coupled to the cold water line 14 to the cold water input 112b. The storage mount 160 may be coupled to the sink 10 adjacent the mounting hole 16, as shown in FIG. 1a.

In use, the oral hygiene device 100 may be mounted in combination with a sink 10, as set forth above, and the piping tees 170 may allow both the sink 10 and the oral hygiene device 100 to be used from a common water supply. The respective flexible tubing 175 provides hot and cold water to the hot and cold water inputs 112a, 112b, and the temperature control 120 determines an amount of hot water passing through the first channel 114a and an amount of cold water passing through the second channel 114b.

For the temperature control embodiment comprising the rotatable disc 125 as discussed above, rotating the disc 125 causes more or less water to flow through the respective channels 114a, 114b. More particularly, rotating the disc 125 fully in the direction 125b causes the first hole 126a to separate from the first channel 114a and the disc 125 to obstruct the first channel 114a, allowing only cold water to pass through the housing 110 (FIG. 4e). Rotating the disc 125 fully in the other direction 125c causes the second hole 126b to separate from the second channel 114b and the disc 125 to obstruct the second channel 114b, allowing only hot water to pass through the housing 110 (FIG. 4g). Additionally, rotating the disc 125 an intermediate amount in either direction 125b, 125c allows various amounts of both hot and cold water to pass through the housing 110. Therefore, by rotating the disc 125, the user can control the temperature of the water passing through the housing 110.

The adjustable volume valve 130 may be used as set forth above to determine an amount of water that exits the outlet 113, and the on-off valve 140 may be used to selectively restrain water from exiting the outlet 113. The valve 130 may allow intermediary amounts of water to pass through the outlet 113, while the valve 140 may act as an on-off switch without further adjusting the water flow.

Once the user has adjusted the temperature and water flow, the nozzle 150 may be positioned inside the user's mouth, and water flowing out the nozzle 150 may be used to clean the mouth cavity, and especially places in the mouth that are otherwise difficult to reach. The housing 110 may be coupled to the storage mount 160 when not in use, and the sleeve 165 may be coupled to the storage mount 160 to enclose the housing 110.

It is understood that while certain forms of this invention have been illustrated and described, it is not limited thereto except insofar as such limitations are included in the following claims and allowable functional equivalents thereof.

The invention claimed is:

1. An oral hygiene device for use with a sink having a hot water line and a cold water line, said device comprising:
   a storage mount;
   a housing removably coupled to said storage mount, said housing having a hot water input and a cold water input and an outlet, said housing having a first channel coupling said hot water input to said outlet and a second channel coupling said cold water input to said outlet, a portion of said first channel corresponding with a portion of said second channel;
   a first piping tee operatively coupled to said hot water line;
   a second piping tee operatively coupled to said cold water line;
   a flexible tube connecting said first piping tee to said housing hot water input;
   a flexible tube connecting said second piping tee to said housing cold water input;
   an adjustable temperature valve in said first channel determining an amount of hot water passing through said first channel;
   another adjustable temperature valve in said second channel determining an amount of cold water passing through said second channel; and
   an adjustable volume valve determining an amount of water exiting said outlet, said volume valve being in said first channel portion that corresponds with said second channel portion.

2. The oral hygiene device of claim 1, further comprising a nozzle operatively coupled to said housing, said nozzle providing a channel extending from said outlet to direct water flow from said outlet through said nozzle, said nozzle having an elongate configuration for positioning inside a user's mouth.

3. The oral hygiene device of claim 2, wherein said nozzle is removably coupled to said housing.

4. The oral hygiene device of claim 3, further comprising a sleeve selectively coupled to said storage mount to enclose said housing when said housing is coupled to said storage mount.

5. The oral hygiene device of claim 1, wherein:
said adjustable temperature valve in said first channel comprises a rotatable disc having a first hole corresponding to said first channel when said disc is at a first position;
said another adjustable temperature valve in said second channel comprises a second hole in said rotatable disc corresponding to said second channel when said disc is at said first position;
rotation of said disc in a first direction causes said first hole to separate from said first channel and said disc to obstruct said first channel; and
rotation of said disc in a second direction causes said second hole to separate from said second channel and said disc to obstruct said second channel.

6. The oral hygiene device of claim 1, wherein:
said adjustable volume valve comprises a rotatable disc having a hole selectively interacting with said first channel portion that corresponds with said second channel portion; and
rotation of said disc causes said hole to separate from said first channel portion and said disc to obstruct said first channel portion.

7. The oral hygiene device of claim 1, further comprising an on-off valve in said housing, said on-off valve selectively restraining water from exiting said outlet.

* * * * *

UNITED STATES PATENT AND TRADEMARK OFFICE
CERTIFICATE OF CORRECTION

PATENT NO. : 8,012,111 B2
APPLICATION NO. : 11/962960
DATED : September 6, 2011
INVENTOR(S) : J. Byron Alexander Page 1 of 1

It is certified that error appears in the above-identified patent and that said Letters Patent is hereby corrected as shown below:

On the title page, Item 73 assignee's name, change "Carolyn Marlow Ream," into --Carolyn Marlow Alexander--.

Signed and Sealed this
Third Day of January, 2012

David J. Kappos
*Director of the United States Patent and Trademark Office*